United States Patent [19]

Bader et al.

[11] Patent Number: 5,106,740

[45] Date of Patent: Apr. 21, 1992

[54] IMMOBILIZATION OF AN ISETHIACYANATE OF A COFACTOR ON A POLYMER

[75] Inventors: Hubert Bader, Mainz; Hans-Ullrich Hoppe, Hofheim Am Taunus; Michael Magerstädt, Liederbach; Merten Schlingmann; Dieter Ulschneider, both of Konigstein/Taunus; Axel Walch, Frankfurt am Main, all of Fed. Rep. of Germany

[73] Assignee: Hoechst Aktiengesellschaft, Frankfurt, Fed. Rep. of Germany

[21] Appl. No.: 622,115

[22] Filed: Dec. 6, 1990

Related U.S. Application Data

[63] Continuation of Ser. No. 236,978, Aug. 26, 1988, abandoned.

[30] Foreign Application Priority Data

Aug. 28, 1987 [DE] Fed. Rep. of Germany ....... 3728772

[51] Int. Cl.$^5$ .................. C12N 11/10; C12N 11/08; C12N 11/04; C07H 17/00
[52] U.S. Cl. .................. 435/178; 435/180; 435/182; 423/366; 536/28; 558/232; 564/17
[58] Field of Search ............... 435/177, 178, 180, 182; 536/28, 29; 423/366; 558/232; 564/17

[56] References Cited

U.S. PATENT DOCUMENTS

| | | | |
|---|---|---|---|
| 4,008,363 | 2/1977 | Re et al. ................. | 435/190 |
| 4,100,029 | 7/1978 | Prosperi et al. ............ | 435/182 |
| 4,182,695 | 1/1980 | Horn et al. ................ | 435/180 X |
| 4,326,031 | 4/1982 | Wendrey et al. ............ | 435/146 |
| 4,443,594 | 4/1984 | Buckmann ................. | 536/27 |
| 4,818,542 | 4/1989 | DeLuca et al. ............. | 424/497 X |

FOREIGN PATENT DOCUMENTS

| | | |
|---|---|---|
| 2631045 | 8/1978 | Fed. Rep. of Germany . |
| 2841414 | 7/1979 | Fed. Rep. of Germany . |
| 2930087 | 2/1981 | Fed. Rep. of Germany . |

OTHER PUBLICATIONS

Woenckhaus et al., "Preparations of Holodehydrogenasis by Covalent Fixation of NAD+-Analogs to Alcohol and Lactate Dehydrogenase," Bioorganic Chemistry 12, pp. 45-57 (1983).

S. Sharma, "The Chemistry of Thiophosgene", Sulfur Reports, vol. 5 (1), Jun. 9, 1986, pp. 1-100.

Per-Olof Larsson et al., Preparation of a NAD(-H)-Polymer Matrix Showing Coengzymic Function of the Bound Pyridine Nucleotide, Biotechnol. and Bioeng., vol. XIII, pp. 393-98 (1971).

Jacob Grunwald et al., Nylon Polyethyleneimine Microcapsules for Immobilizing Multienzymes with Soluble Dextran-Nad+ for the Continuous Recycling of the Microencapsulated Dectran-Nad+, Biochem. and Biophys. Res. Comm., vol. 81, No. 2, (1978) pp. 565-570.

Hans-Ludwig Schmidt et al., Coenzyme Properties of NAD+Bound to Different Matrices Through the Amino Group in the 6-Position, Euro. J. Biochem. 67, pp. 295-302 (1976).

*Primary Examiner*—David M. Naff
*Attorney, Agent, or Firm*—Finnegan, Henderson, Farabow, Garrett and Dunner

[57] ABSTRACT

A cofactor having an aromatic or benzylic amino group is converted into an isothiocyanate by reaction with a compound such as thiophosgene and the isothiocyanate of the cofactor is attached to a polymer which is preferably water-soluble. When the polymer has amino groups, a thiourea bridge is formed between the polymer and cofactor and a polymer having hydroxyl groups results in a thiocarbamate bridge. The polymer may be a copolymer of vinylamine or vinylmethylamine and vinylmethylacetamide, partially alkylamine-substituted α, β-poly-(2-hydroxyethyl)-D,L-aspartamide, polyethyleneimine or carbohydrate. The cofactor bound to a polymer and an enzyme are contained in microcapsules or in a membrane to form an enzyme reactor.

9 Claims, No Drawings

IMMOBILIZATION OF AN ISETHIACYANATE OF A COFACTOR ON A POLYMER

This application is a continuation of application Ser. No. 07/236,978, filed Aug. 26, 1988, now abandoned.

The invention relates to an improved process for the immobilization, on polymers, of the cofactors required for enzymatic reactions, and to an enzyme reactor which, besides one or more enzymes, contains one or more cofactors immobilized according to the invention on a polymer.

It is known that enzymatic reactions have acquired increasing importance, because of their high selectivity and good yields, in the preparation of valuable chemical compounds. This entails enzymes being immobilized by various processes and then used as heterogeneous catalysts. They can then easily be removed from the reaction mixture and reused.

Where enzymes or enzymatic complexes are active only in the presence of a low molecular weight cofactor, the task has been likewise to immobilize the cofactor, because otherwise it would have to be continuously added anew to the reaction mixture. It would not be possible to remove a readily soluble low molecular weight cofactor from the reaction product by simple membrane filtration, which would result in complete loss of the costly cofactor with, at the same time, contamination of the final product obtained. This is why many investigations into the immobilization of such cofactors on polymers have been described (cf. P.-O. Larsson and K. Mosbach, Biotechnol. Bioeng. 13 (1971), 393; J. Grunwald and Th. M. S. Chang, Biochem. Biophys. Res. Commun. 81 (1978), 565; German Patent 26 31 045; German Patent 28 41 414; German Offenlegungsschrift 29 30 087).

Cofactors having an adenine ring system such as nicotinamide-adenine dinucleotide ($NAD^+/NADH$), nicotinamide-adenine dinucleotide phosphate ($NADP^+/NADPH$), adenosine monophosphate (AMP), adenosine diphosphate (ADP), adenosine triphosphate (ATP), flavine-adenine dinucleotide ($FAD/FADH_2$) and coenzyme A which are covalently bonded to solid supports or to soluble polymers are already used on a large scale. Thus, cofactors bound to solid supports are employed as ligands in affinity chromatography. Water-soluble polymers with covalently bonded cofactors are very useful in affinity partition. Cofactors such as $NAD^+/NADH$ and $NADP^+/NADPH$ can be regenerated and used in enzymatic systems under recycling conditions.

The procedure for the preparation of cofactors which contain an adenine ring system and are bound to polymers is such that, firstly, the nitrogen atom in the 6 position is connected to a reactive group which can then in turn react with a functional group of the macromolecule. This entails, firstly, the adenine ring system being reacted on the N(1) atom with an alkylating agent which has another functional group which is intended to allow reaction with the macromolecule. Suitable alkylating agents are halogeno carboxylic acids such as iodoacetic acid, epoxides such as 3,4-epoxybutyric acid, lactones such as propionolactone or aziridines such as ethyleneimine.

In the case of AMP, ADP and ATP, the alkylation is followed immediately by a Dimroth rearrangement to give the N(6) form. The Dimroth rearrangement is then followed by reaction with the macromolecule. In the case of $NAD^+$ and $NADP^+$, a reduction is carried out before the Dimroth rearrangement, and a reoxidation of the nicotinamide ring is carried out after the Dimroth rearrangement.

However, it has already been disclosed in German Patent 28 41 414 that these reaction sequences necessary for immobilizing cofactors on polymers are unsatisfactory, because the large number of reactions which are needed reduce the yields, and in this way it is possible to immobilize the costly cofactor only in an amount of 12 to 40% on the polymer. For this reason, it is proposed therein to improve the yield by not subjecting the adenine derivatives alkylated in the 1 position to a Dimroth rearrangement until after the addition onto the polymer. Although it is possible in this way to reduce the losses in yields, the number of reaction steps which are required remains the same, and it is still necessary with the $NAD^+$ and $NADP^+$ derivatives to carry out a reduction and a reoxidation of the nicotinamide ring.

Hence the object was to simplify the process for binding the cofactors to polymers, in order to reduce losses of yields and of activity of the costly cofactors.

This object is achieved according to the invention by cofactors which have aromatic or benzylic amino groups being firstly converted, for example by reaction with thiophosgene, into the corresponding isothiocyanate, and the latter then being added onto a suitable polymer having functional groups. For example, use of NADH as cofactor and of a polymer having amino groups results in thiourea derivatives of the general formula

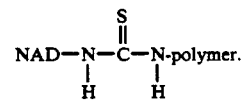

Use of a polymer having hydroxyl groups results in the corresponding thiocarbamates. The preparation of thioureas and thiocarbamates from isothiocyanates and compounds having amino or hydroxyl groups is state of the art (cf. L. Drobnica, P. Krisian, J. Augustin in "The Chemistry of Functional Groups" (Patai, Ed.) part 2: "Cyanates and their Derivatives", Wiley, New York, Chapter 22, 1003).

The polymer to be chosen for binding the cofactor ought to be soluble in water, because if the cofactor is bound to a polymer which is insoluble in water it is no longer possible for the bound $NAD^+$ to be reduced completely, and this results in considerable losses of activity (cf. H. -L. Schmidt and G. Grenner, Eur. J. Biochem. 67, 295-302 (1976)).

The polymers preferred for the immobilization of the cofactors are soluble in water and have primary or secondary amino groups. Copolymers of vinylamine and vinylmethylacetamide or vinylmethylamine and vinylmethylacetamide have proven particularly appropriate, it being possible to vary the ratio of the monomers between 1:99 and 40:60% by weight.

To prepare these copolymers, N-vinylformamide or N-vinyl-N-methylformamide is reacted with other water-soluble N-vinylamides such as N-vinyl-N-methylacetamide or N-vinylpyrrolidone, and the N-vinylformamide or N-vinyl-N-methylformamide units which have been incorporated are hydrolyzed with strong acids, preferably hydrochloric acid, in aqueous solution to give N-vinylamine or N-vinyl-N-methylamine chain members. The formamides are very readily hydrolyzed, in contrast to other vinylamides, and consequently the other N-vinylamides which have been polymerized in are not simultaneously hydrolyzed to a noteworthy extent. Finally, the formic acid which has been eliminated, and the hydrochloric acid which has been employed, are removed by ion exchange.

The base component can be adjusted as desired by varying the amount of N-vinylformamide or N-vinyl-N-methylformamide polymerized in. If N-vinylformamide is employed for the copolymerization, the final product contains N-vinylamine units, and when N-vinyl-N-methylformamide is copolymerized the final product contains N-vinyl-N-methylamine chain members. However, it is also possible to carry out a terpolymerization, for example of N-vinylformamide, N-vinyl-N-methylformamide and N-vinyl-N-methylacetamide. Hydrolysis of these polymers permits access to polymeric support substances having primary and secondary vinylamine units, that is to say different base reactivities, which are likewise suitable for the immobilization of cofactors.

Very similar polymers are also obtained by partial hydrolysis of poly-N-vinylformamide or poly-N-vinyl-N-methylformamide homopolymers. It is likewise possible in these cases to adjust the base content as desired by varying the amount of acid and the hydrolysis time. It is also possible, by copolymerization of N-vinylformamide and N-vinyl-N-methylformamide, followed by partial hydrolysis, to synthesize water-soluble polymeric support substances with different base reactivities.

The adjustment of a desired mean molecular size of the basic, water-soluble support substances can be influenced to a large extent (MW 10,000 to 500,000) by a number of measures, such as choice of the polymerization temperature, of the solvent and of the initiator concentration.

Experience has likewise been good with the partially alkylamine-substituted $\alpha,\beta$-poly-(2-hydroxyethyl)-D,L-aspartamide.

However, it is also possible to employ other water-soluble polymers which have functional groups reacting with isothiocyanates. For example, it is also possible to use polyethyleneimine or water-soluble carbohydrates.

Using the process according to the invention, cofactors are successfully immobilized in virtually quantitative yield, and without loss of activity, on polymers and, moreover, the multistage reaction sequence hitherto regarded as necessary is avoided. The cofactors immobilized on polymers in this way can be employed in a variety of ways. For example, they can be enclosed together with one or more enzymes in microcapsules. The preparation of microcapsules of this type having a semipermeable wall which allows substrate and reaction product to pass through but retains the enzyme(s) and the bound cofactor has long been state of the art (cf. Th. M. S. Chang, Biomedical Appl., Immobilized Enzyme Proteins, Vol. 1 (1977), 69, Plenum, New York 1977).

The enzymes can also be used, together with the cofactor immobilized on a polymer, in a membrane reactor equipped with an ultrafiltration membrane, which membrane serves to retain the employed enzymes and the cofactor in the reactor but to allow the low molecular weight product and the unreacted substrate to pass through. Membrane reactors of this type are also now state of the art and are described, for example, in German Offenlegungsschrift 29 30 078.

An enzymatic reaction can be carried out continuously, both with semipermeable microcapsules and in an ultrafiltration cell, if the cofactor(s) catalyze several reactions successively and are, during this, returned to their initial state. For example, $NAD^+$ can convert, with the aid of malic dehydrogenase, malate into oxalacetate. The NADH produced during this can then reduce, with the aid of alcohol dehydrogenase, acetaldehyde to ethanol. Thereafter $NAD^+$ is again present and available for another reduction. Thus, a system of this type undergoes continual regeneration and can in theory carry out this reaction for an unlimited period. However, in practice it is found that these systems composed of several enzymes and cofactors gradually lose their activity. As is made clear by the experiments described in detail in the examples, however, no loss of activity has been observed with the enzyme reactors prepared according to the invention. An additional factor is that the cofactor is immobilized according to the invention in a simple one-pot reaction and in virtually quantitative yield.

EXAMPLE 1

Preparation of 6-isothiocyanato-nicotinamide-adenine dinucleotide ("NAD-NCS")

2 mmol of $NAD^+$ were dissolved in 10 ml of $H_2O$ in a round-bottomed flask with attached bubble-counter, and a little $Na_2CO_3$ was added. A solution of 20 mmol of thiophosgene in 10 ml of $CHCl_3$ was added with vigorous stirring at 20° C. The pH was checked every 10 minutes and kept between 5.5 and 8.5 by the addition of small amounts of sodium carbonate. After 3.5 hours there was no longer any change in the pH, and no further gas was evolved. The mixture was evaporated to dryness in vacuo and freeze-dried. The slightly brownish product mixture could be purified of by-products by column chromatography on silica gel using water/acetonitrile as eluent. However, it is advisable to use the product mixture unpurified for the reaction with the polymer (see Example 2), since purification by ultrafiltration of the product immobilized on the polymer is considerably more straightforward and, moreover, the sensitivity of NAD-NCS results in losses due to dimerization and trimerization during purification.

EXAMPLE 2

Reaction of vinylamine/vinylmethylacetamide copolymer (4.8:95.2% by weight) with 6-isothiocyanato-nicotinamideadenine dinucleotide (NAD-NCS)

10 ml of a solution of 2 mmol of NAD-NCS in 20 ml of water were added to 863 mg of polymer ($\triangleq$1 mmol of $NH_2$ groups) in 5 ml of $H_2O$ in a 50 ml round-bottomed flask at 20° C., the pH was adjusted to 8 with 1N NaOH, and the solution was stirred at 20° C. for 15 hours. The solution was then subjected to ultrafiltration through a cellulose acetate membrane (exclusion limit: molecular weight 5,000) in an ultrafiltration cell under an excess pressure of 3 bar, making up with 50 ml of water each time, and filtering again, 10 times. The retentate and the 10 permeates were measured in a UV spectrometer at $\lambda=257$ nm (measurement of absorption). The permeates showed and adsorption which became smaller as ultrafiltration progressed, i.e. a decreasing $NAD^+$ content. The retentate contained 70 to 90% of the NAD+ employed. This result was confirmed by measurement of the absorption of a weighed sample of the freeze-dried retentate dissolved in water, and comparison with a calibration plot constructed with pure NAD+. Freeze-drying of the retentate yielded 12 g of product (85% based on polymer).

The product was employed in place of NAD+ as cofactor in the standard assay of Boehringer Mannheim for the determination of malate using malic dehydrogenase, of ethanol using alcohol dehydrogenase and of lactate using lactic dehydrogenase. In all cases the enzyme activity, and thus the cofactor activity too, was unchanged when NAD+ was replaced by an equivalent amount of the NAD+ immobilized on a polymer.

EXAMPLE 3

Coupling of
α,β-poly-(2-hydroxyethyl)-D,L-aspartamide partially substituted with aminoethyl groups ($H_2N$-PHEA) to NAD-NCS via these amino groups The $H_2N$-PHEA contained $10^{-4}$ mol/g amino groups. Since, under the conditions used here, it is principally the amino groups which react with the isothiocyanate, NAD-NCS was employed stoichiometric to this number of amino groups. 1.5 g of polymer ($1.5 \times 10^{-4}$ mol of amino groups) were dissolved in about 25 ml of $H_2O$ in a 100 ml round-bottomed flask at 20° C., and a solution of $1.4 \times 10^{-4}$ mol of NAD-NCS was added. The pH was adjusted to 8 with NaOH. The mixture was stirred at 20° C. for 20 h and then subjected to ultrafiltration at 3 bar through a cellulose acetate membrane (exclusion limit: molecular weight 5,000), making up with 60 ml of water each time, and filtering again, 6 times. The content of NAD+ in the product was determined by comparing the UV absorption of the permeates and of the retentate at 257 nm. It was 80% of the amount employed. The retentate was freeze-dried, total yield 1.4 g (92%), so that the effective yield of confugation emerges as 87%.

EXAMPLE 4

Microencapsulation of an enzyme system with NAD immobilized on a polymer

The enzyme system employed was malic dehydrogenase (MDH) in conjunction with glutamic-oxalacetic transaminase (GOT), in analogy to the malate assay marketed by Boehringer Mannheim. This entailed L-malate being converted by MDH with NAD+ to oxalacetate, NADH and H+. In order to displace the equilibrium away from L-malate, the oxalacetate was converted into L-aspartate and α-ketoglutarate by GOT and addition of glutamate.

In a typical experiment, 0.01 ml of a 5 mg/ml solution of MDH, 0.01 ml of a 2 mg/ml suspension of GOT (both in water) and 25.5 mg of the NAD+-polymer ($\triangleq$10 mg of NAD+) described in Example 2 were made up to 1.42 ml with water. 0.3 ml of this solution was mixed with 1 g of a 2% strength aqueous solution of alginate 20/60, and the mixture was sprayed using a syringe and needle (internal diameter 0.2 mm) into a 0.4% strength aqueous solution of polylysine, average molecular weight 5800. 558 mg of microcapsules were obtained from 931 mg of sprayed solution and were removed from the polylysine solution after 15 minutes (decantation) and then washed with 1% strength aqueous NaCl solution. The capsules were then placed for 1 minute in a 12.5% strength glutaraldehyde solution and thus crosslinked. The capsules were placed in water in a 400 ml beaker and agitated by blowing in nitrogen. Aliquots of the supernatant solution were taken after 17 hours, 2 days, 3 days, 6 days and 7 days, and the UV absorption of the solution at 257 nm was measured and compared with a NAD+ calibration plot and thus the NAD+ content of the supernatant solution (i.e. the NAD+ lost from the capsules) was determined. The results of this were as follows:

| Time | NAD+ lost from the capsules | |
|---|---|---|
| 17 h | 1.6% | a few mechanically damaged capsules are visible to the naked eye |
| 2 days | 1.7% | |
| 3 days | 0.8% | |
| 4 days | 0.8% | |
| 7 days | 0.4% | |

After 9 days, 44 capsules, corresponding to about $0.7 \times 10^{-3}$ mmol of NAD+, were removed and used to convert malate under the conditions described in the malate assay of Boehringer Mannheim. The conversion achieved by the microcapsules was 0.004 mg from an excess of malate with an equivalent amount of NAD+ within 30 minutes (theoretical conversion 0.003 mg of L-malate).

EXAMPLE 5

Semicontinuous enzyme reactor with NAD immobilized on a polymer, with regeneration of the cofactor by recycling The enzyme system employed for this was formic dehydrogenase (FDH) and lactic dehydrogenase (LDH), with formate being converted by FDH with NAD+ into $CO_2$ and NADH, and pyruvate being converted by LDH with NADH into lactate. Pyruvate and formate were used in excess as substrates, $CO_2$ escaped, and lactate was determined as the only product of the reaction in solution. The ultrafiltration membrane used for retention of the enzymes and of the NAD-polymer was composed of cellulose acetate (exclusion limit molecular weight 5000). The reaction was carried out in an ultrafiltration cell with the reaction mixture being under a pressure of 2 bar, and it being possible to determine the lactate in the fractions of permeate taken.

NAD-polymer from Example 2 (corresponding to 0.021 mmol of NAD), 0.1 mg of LDH, 4 units of FDH, 0.26 mmol of pyruvate and 0.26 mmol of formate in 3.7 ml of phosphate buffer, pH 7.2, were employed. The permeate fractions were collected every 30 minutes while stirring under an excess pressure of 2 bar of $N_2$. After each fraction, the concentrate was made up to the original 3.7 ml with phosphate buffer, pH 7.2. In addition, after every 4th fraction, 0.26 mmol of pyruvate and 0.26 mmol of formate were added. The permeates were examined for the lactate content using the lactate determination assay marketed by Boehringer Mannheim. The lactate yield obtained in each permeate fraction (1 ml each) was from 3 to $6 \times 10^{-4}$ mmol of lactate over 22 fractions. After the test had been interrupted and continued after 2 days (weekend) the lactate content in each permeate fraction remained at the same constant level.

EXAMPLE 6

A. Preparation of an N-vinylamine/N-vinyl-N-methylacetamide copolymer, N-vinylamine content 4.8% by weight 36 g of N-vinyl-N-methylacetamide and 3 g of N-vinylformamide were copolymerized in 40 ml of isopropanol using 400 mg of α,α'-azoisobutyronitrile as initiator at 80° C. (24 h).

The isopropanol was subsequently removed by distillation, water (40 ml) simultaneously being added. 40 ml of concentrated hydrochloric acid were added to the resulting aqueous polymer solution, and it was heated at 110° C. for 8 h. The strongly acid reaction mixture was diluted with water, and subsequently hydrochloric and formic acids were removed on a strongly basic ion exchanger. Concentration in vacuo (~100 mbar) resulted in an aqueous solution of a N-vinylamine/N-vinyl-N-methylacetamide copolymer with an N-vinylamine content of ~4.8% by weight. The solids content of the polymer solution was 33.3%, the pH was 11.5, and the reduced viscosity of the polymer was determined as 0.25 dl/g (measured on a 1% strength solution in $H_2O$ at 25° C.).

B. Preparation of an N-vinylamine/N-vinylpyrrolidone copolymer, N-vinylamine content 5.7% by weight.

20 g of N-vinylpyrrolidone and 2 g of N-vinylformamide were polymerized in 120 ml of water, to which 1 ml of $NH_4OH$ solution was added, at 80° C. under a blanket of argon. Initiator α,α'-azoisobutyronitrile 110 mg, polymerization time 24 h. 145 ml of concentrated hydrochloric acid were added to the resulting aqueous copolymer solution, and the mixture was refluxed (110° C.) for 7 h. The mixture was subsequently worked up as described in A using a strongly basic ion exchanger. 160 g of aqueous solution of an N-vinylamine/N-vinylpyrrolidone copolymer with an N-vinylamine content of 5.7% by weight were then obtained. The solids content of the polymer solution was 9.53%, the pH was 10.1, and the reduced viscosity of the polymer was determined as 1.61 dl/g (measured on a 1% strength solution in $H_2O$ at 25° C.).

C. Preparation of N-vinyl-N-methylamine/N-vinyl-N-methylformamide copolymers (by process B)

N-vinyl-N-methylformamide was polymerized with α,α'-azoisobutyronitrile as initiator, and the homopolymer was only partially hydrolyzed with hydrochloric acid in aqueous solution at 100° C. The results of the partial hydrolysis as a function of the time and of the hydrochloric acid concentration are to be found in the Table which follows:

| Hydrolysis | Process (a) | Process (b) |
| --- | --- | --- |
| ½ hour | 9.5% basic N | 13.5% basic N |
| 2 hours | 15.7% basic N | 20.1% basic N |

In process (a) one mol of HCl is employed for one mol of N-vinyl-N-methylformamide, and in process (b) 2.5 mol of HCl are employed for one mol.

The figures for basic nitrogen were determined after removal of formic and hydrochloric acids using an ion exchanger; 100% hydrolysis corresponds to a figure of 24.9% for basic nitrogen. An N-vinyl-N-methylamine/N-vinyl-N-methylformamide copolymer with 9.0% basic nitrogen, for example, has an N-vinyl-N-methylamine content of 36.0% by weight.

What is claimed is:

1. A process for binding cofactors to polymers, which comprises the steps of:
   (a) converting a cofactor which has aromatic or benzylic amino groups into its corresponding isothiocyanate by reacting the cofactor with thiophosgene to convert the cofactor into the isothiocyanate; and
   (b) attaching the isothiocyanate from step (a) to a water-soluble polymer having functional groups capable of reaction with the isothiocyanate, by reacting the isothiocyanate with the polymer.

2. The process of claim 1, wherein the water soluble polymer has primary or secondary amino groups.

3. The process of claim 2, wherein the water-soluble polymer is a copolymer of vinylamine and vinylmethylacetamide or is a copolymer of vinylmethylamine and vinylmethylacetamide, with the ratio of the monomers being between 1:99 and 40:60% by weight.

4. The process of claim 2, wherein the water-soluble polymer is a partially alkylamine-substituted α,β-poly-(2-hydroxyethyl)-D,L-aspartamide.

5. The process of claim 1, wherein the water-soluble polymer is polyethyleneimine or a water-soluble carbohydrate.

6. A cofactor which is bound via an aromatic or benzylic amino group to a water-soluble polymer by means of a thiourea or thiocarbamate bridge prepared by the process of claim 1.

7. The cofactor bound to a polymer according to claim 6 wherein the bound cofactor is combined with one or more enzymes to form an enzyme reactor.

8. The cofactor bound to a polymer combined with enzymes according to claim 7, wherein the cofactor bound to the polymer and the enzymes are contained in microcapsules.

9. The cofactor bound to a polymer combined with enzymes according to claim 7, wherein the cofactor bound to the polymer and the enzymes are contained in a membrane reactor equipped with an ultrafiltration membrane.

* * * * *